United States Patent
Lee et al.

(10) Patent No.: US 11,097,073 B2
(45) Date of Patent: Aug. 24, 2021

(54) NOSE-TO-BRAIN DRUG DELIVERY DEVICE

(71) Applicant: IUCF-HYU (INDUSTRY-UNIVERSITY COOPERATION FOUNDATION HANYANG UNIVERSITY), Seoul (KR)

(72) Inventors: Sang-Kyung Lee, Seoul (KR); Kun Ho Chung, Seoul (KR); Irfan Ullah, Seoul (KR); Priti Kumar, Hamden, CT (US); Sangah Lee, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 256 days.

(21) Appl. No.: 16/193,696

(22) Filed: Nov. 16, 2018

(65) Prior Publication Data

US 2019/0151573 A1    May 23, 2019

Related U.S. Application Data (63) Continuation of application No. PCT/KR2017/005017, filed on May 15, 2017.

(30) Foreign Application Priority Data

May 17, 2016  (KR) .................. 10-2016-0059895
May 15, 2017  (KR) .................. 10-2017-0059980

(51) Int. Cl.
*A61M 11/02*    (2006.01)
*A61M 15/08*    (2006.01)
(Continued)

(52) U.S. Cl.
CPC .......... *A61M 11/02* (2013.01); *A61M 11/002* (2014.02); *A61M 11/007* (2014.02);
(Continued)

(58) Field of Classification Search
CPC .... A61M 11/00; A61M 11/02; A61M 11/007; A61M 15/08; A61M 15/009;
(Continued)

(56) References Cited

U.S. PATENT DOCUMENTS 5,765,552 A    6/1998   Zanen et al.
7,934,503 B2 *  5/2011  Djupesland ........... B05B 11/061
                                                        128/207.18
(Continued)

FOREIGN PATENT DOCUMENTS

KR       10-0627592 B1    9/2006
KR    10-2014-0003582 A    1/2014

OTHER PUBLICATIONS

International Search Report for PCT/KR2017/005017 dated Aug. 8, 2017 [PCT/ISA/210].

*Primary Examiner* — Laura A Bouchelle
(74) *Attorney, Agent, or Firm* — Sughrue Mion, PLLC (57) ABSTRACT

A nose-to-brain drug delivery device is provided. The nose-to-brain drug delivery device includes a freeze-dried drug container for storing a freeze-dried drug, a restoring solvent container for storing a solvent for thawing the freeze-dried drug, a membrane for preventing the freeze-dried drug from being mixed with the solvent, and a compressor for providing a driving force. The membrane is opened by the driving force of the compressor to mix the freeze-dried drug with the solvent, thereby thawing the freeze-dried drug, and the thawed drug is sprayed by the driving force of the compressor.

8 Claims, 9 Drawing Sheets
(3 of 9 Drawing Sheet(s) Filed in Color)

(51) Int. Cl.
*A61M 11/00* (2006.01)
*A61M 15/00* (2006.01)
*B05B 11/00* (2006.01)
*A61M 31/00* (2006.01)

(52) U.S. Cl.
CPC ........ *A61M 11/008* (2014.02); *A61M 15/003* (2014.02); *A61M 15/0031* (2014.02); *A61M 15/08* (2013.01); *B05B 11/00* (2013.01); *A61M 15/0003* (2014.02); *A61M 15/009* (2013.01); *A61M 15/0021* (2014.02); *A61M 31/00* (2013.01); *A61M 2202/04* (2013.01); *A61M 2202/064* (2013.01); *A61M 2205/8206* (2013.01); *A61M 2205/8225* (2013.01); *A61M 2206/14* (2013.01); *A61M 2206/16* (2013.01); *A61M 2210/0693* (2013.01)

(58) Field of Classification Search
CPC .. A61M 3/005; A61M 5/3015; A61M 5/2066; A61M 5/2448; A61M 5/284; A61M 2210/0693; B05B 11/04; B05B 11/048
See application file for complete search history.

(56) References Cited

U.S. PATENT DOCUMENTS

| | | | |
|---|---|---|---|
| 8,377,009 B2* | 2/2013 | Sullivan | A61M 11/06 604/200 |
| 9,550,036 B2* | 1/2017 | Hoekman | A61M 11/007 |
| 2004/0045546 A1 | 3/2004 | Hirsh et al. | |
| 2012/0085344 A1 | 4/2012 | Luber et al. | |
| 2013/0142868 A1* | 6/2013 | Hoekman | A61M 15/009 424/450 |
| 2014/0014104 A1 | 1/2014 | Hoekman et al. | |
| 2014/0343494 A1 | 11/2014 | Hoekman et al. | |
| 2015/0231130 A1 | 8/2015 | Wynne et al. | |

* cited by examiner

NOSE-TO-BRAIN DRUG DELIVERY DEVICE

CROSS-REFERENCE TO RELATED APPLICATION

This application is a continuation of pending International Application No. PCT/KR2017/005017, which was filed on May 15, 2017 and claims priority to Korean Patent Application Nos. 10-2016-0059895 and 10-2017-0059980, filed on May 17, 2016 and May 15, 2017, in the Korean Intellectual Property Office, the disclosures of which are hereby incorporated by reference in their entireties.

BACKGROUND

1. Field

The present disclosure relates to a drug delivery device, and more particularly, to a nose-to-brain drug delivery device which stores a freeze-dried drug and thaws the freeze-dried drug to spray the thawed drug together with a solute.

2. Description of the Related Art

In a healthcare field, a drug delivery system (DDS) may control delivery and release of materials with pharmacological activity into cells, tissues, and/or organs by using various physiochemical techniques for optimal effects. In other words, the drug delivery system may be developed for maintenance of the effects of the drug in a living body, maintenance of a suitable concentration of the drug in the living body, and the orientation of the drug to a target. As interest in health increases, effective and economical treatments for various diseases are being required. Thus, the drug delivery system may be converted into a customized medication system in which a required amount of a drug is administered when and where it is needed, depending on the individual's condition.

The drug delivery systems may be classified depending on a delivery path, a kind of a drug, and a delivery technique. Depending on the delivery path, the drug delivery systems may be classified into an oral drug delivery system, a syringe-type drug delivery system, a lung-inhalation drug delivery system, a percutaneous drug delivery system, a mucosal drug delivery system, and an insertion drug delivery system. In addition, the drug delivery systems may be classified into an absorption-promoting drug delivery system, a drug-sustaining delivery system, and a target-concentrated drug delivery system, depending on the application.

A pressurized olfactory delivery (POD) device among the drug delivery systems may prevent gastrointestinal protease degradation caused by oral administration, may relatively easily inject a drug, and may be used instead of a syringe. In particular, techniques for directly delivering a drug to a brain through a nasal cavity (nose-to-brain) are actively studied in connection with the POD device. The nasal cavity (or the nose) may be the only area where neurons of the brain are exposed outward, and thus it may be a spot through which a drug is effectively injected to the brain.

However, the injection of the drug to the brain through the nasal cavity (or the nose) may be difficult by a blood-brain barrier existing on a path from the nasal cavity toward the brain.

Thus, new drug delivery devices for delivering a drug to a brain through a nasal cavity are being studied.

Patent Document: U.S. Publication No. US20140343494

SUMMARY

The present disclosure may provide a drug delivery device with excellent drug preservation effect.

The present disclosure may also provide a drug delivery device capable of easily storing a freeze-dried drug and of easily spraying the freeze-dried drug.

The present disclosure may further provide a drug delivery device capable of easily exchanging a drug.

In an aspect, a nose-to-brain drug delivery device includes a freeze-dried drug container for storing a freeze-dried drug, a restoring solvent container for storing a solvent for thawing the freeze-dried drug, a membrane for preventing the freeze-dried drug from being mixed with the solvent, and a compressor for providing a driving force. The membrane is opened by the driving force of the compressor to mix the freeze-dried drug with the solvent, thereby thawing the freeze-dried drug, and the thawed drug is sprayed by the driving force of the compressor. The thawed drug is sprayed into a nose of a subject in a mecca position state where a head of the subject faces a chest of the subject.

In an embodiment, the restoring solvent container may be formed of a flexible material and may be deformed by the driving force to increase an internal pressure of the restoring solvent container, and the membrane may be opened by the increased internal pressure.

In an embodiment, the restoring solvent container may be moved in a direction toward the freeze-dried drug container by the driving force to increase an internal pressure of the restoring solvent container, and the membrane may be opened by the increased internal pressure.

In an embodiment, the compressor may provide the driving force to one end of the restoring solvent container, and another end of the restoring solvent container may be blocked by the membrane so as to be separated from the freeze-dried drug container.

In an embodiment, the one end of the restoring solvent container may include a receiving recess provided with the driving force.

In an embodiment, the freeze-dried drug container may include a fine hole for spraying the thawed drug.

In an embodiment, the nose-to-brain drug delivery device may further include a spray unit. The drug released from the fine hole may be sprayed outward through the spray unit.

In an embodiment, the restoring solvent container, the membrane, and the freeze-dried drug container may be disposed in the order named, from the compressor.

In an embodiment, the nose-to-brain drug delivery device may further include a first housing in which the compressor is received, and a second housing in which the restoring solvent container, the membrane, and the freeze-dried drug container are received. The second housing may be detachable from the first housing, and a longitudinal direction of the first housing may form an acute angle with a longitudinal direction of the second housing when the first housing is coupled to the second housing.

In an aspect, a nose-to-brain drug delivery device includes a freeze-dried drug container for storing a freeze-dried drug, a restoring solvent container for storing a solvent for thawing the freeze-dried drug, and a membrane between the freeze-dried drug container and the restoring solvent container. The membrane prevents the freeze-dried drug from being mixed with the solvent in a drug storing mode and is opened in a drug spraying mode to mix the freeze-dried drug with the solvent, thereby thawing the freeze-dried drug. The thawed drug is sprayed into a nose of a subject in a mecca position state where a head of the subject faces a chest of the subject.

In an aspect, a nose-to-brain drug delivery device includes a freeze-dried drug container for storing a freeze-dried drug, a restoring solvent container for storing a solvent for thawing the freeze-dried drug, a membrane for preventing the freeze-dried drug from being mixed with the solvent, and a compressor for providing a driving force. The membrane is opened by the driving force of the compressor to mix the freeze-dried drug with the solvent, thereby thawing the freeze-dried drug, and the thawed drug is sprayed by the driving force of the compressor. A spray pressure of the thawed drug ranges from 6 psi to 20 psi.

In an embodiment, the spray pressure of the thawed drug may range from 6 psi to 15 psi.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being "on" another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term "and/or" includes any and all combinations of one or more of the associated listed items.

The terminology used herein is for the purpose of describing particular embodiments only and is not intended to limit the invention. As used herein, the singular terms "a", "an" and "the" are intended to include the plural forms as well, unless the context clearly indicates otherwise. It will be further understood that the terms "comprises", "comprising", "includes", "including", "have", "has" and/or "having" when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being "connected" or "coupled" to another element, it may be directly connected or coupled to the other element or intervening elements may be present.

In addition, in explanation of the present invention, the descriptions to the elements and functions of related arts may be omitted if they obscure the subjects of the inventive concepts.

Figure 1:
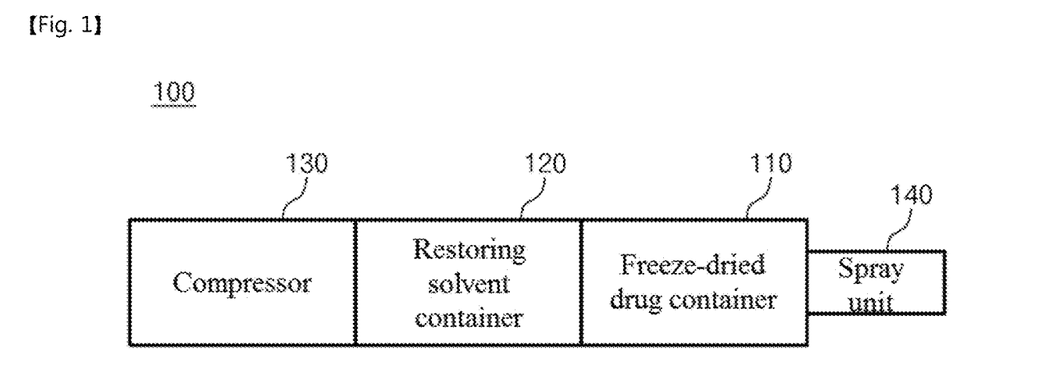
FIG. 1 is a block diagram for explaining a function of a drug delivery device according to an embodiment of the inventive concepts.

FIG. 1 is a block diagram for explaining a function of a nose-to-brain drug delivery device according to an embodiment of the inventive concepts. Hereinafter, the nose-to-brain drug delivery device will be abbreviated as a drug delivery device for the purpose of ease and convenience in explanation.

Referring to FIG. 1, a drug delivery device 100 according to an embodiment of the inventive concepts may include a freeze-dried drug container 110, a restoring solvent container 120, a compressor 130, and a spray unit 140. Hereinafter, each of the components will be described.

The freeze-dried drug container 110 may store or contain a drug in a freeze-dried state. It may be understood that when a drug is freeze-dried, it may be frozen and then solid water may be sublimated into a gas by lowering the ambient pressure. In other words, the freeze-dried drug container 110 may store a drug in freeze-dried powder form.

The freeze-dried drug container 110 may store various kinds of freeze-dried drugs, and the various kinds of drugs may include, but not limited to, a dementia drug, a Parkinson drug, a depression drug, a cancer drug, and an ischemic drug. In some embodiments, the freeze-dried drug container 110 may store at least one of insulin, oxytosin, glutathione, ketamine, histone deacetylase inhibitors (HDAC inhibitors, HDCAi), paclitaxel, or taxol in freeze-dried form.

The restoring solvent container 120 may store a restoring solvent for thawing the freeze-dried drug. Hereinafter, the restoring solvent may be abbreviated as a solvent for the purpose of ease and convenience in explanation.

The restoring solvent container 120 may store at least one of, for example, glycerol, propylene glycol, polyethylene glycol, polypropylene glycol, ethyl alcohol, isopropyl alcohol, peanut oil, sterile water, a sterile normal saline solution, or a sterile phosphate buffer solution, as the restoring solvent.

In a drug storing mode, a membrane may prevent the freeze-dried drug of the freeze-dried drug container 110 from being mixed with the restoring solvent of the restoring solvent container 120. On the contrary, in a drug spraying mode, the membrane may be opened to mix the freeze-dried drug of the freeze-dried drug container 110 with the restoring solvent of the restoring solvent container 120, and thus the freeze-dried drug may be thawed and restored.

The compressor 130 may provide a driving force to the drug delivery device 100. In more detail, the compressor 130 may provide the driving force to spray the drug and may also open (i.e., break) the membrane between the freeze-dried drug container 110 and the restoring solvent container 120 to mix the freeze-dried drug and the restoring solvent.

The compressor 130 may be driven by at least one of various methods. In an embodiment, the compressor 130 may be a syringe type and may provide the driving force by an operator. Alternatively, the compressor 130 may include a compressed gas and may inject the compressed gas by operation of an operator to provide the driving gas. In this case, for example, when an operator presses a button provided on one side of the drug delivery device 100, the compressed gas may be provided at a predetermined pressure. Hereinafter, the embodiment in which the compressor 130 includes the compressed gas will be described for the purpose of ease and convenience in explanation.

The compressed gas may be formed of a material harmless to the human body even though it is inhaled into the human body. For example, the compressed gas may include at least one of hydrofluoroalkane (HFA), nitrogen, cholorofluorocarbon (CFC), or air.

The compressed gas may not be in the form of a compressed gas but may be provided in the form of compressed liquid.

The spray unit 140 may provide a path through which the drug thawed by mixing the freeze-dried drug with the restoring solvent is sprayed by the driving force provided from the compressor 130.

Hereinafter, overall components of a drug delivery device according to an embodiment of the inventive concepts will be described with reference to FIG. 2.

Figure 2:
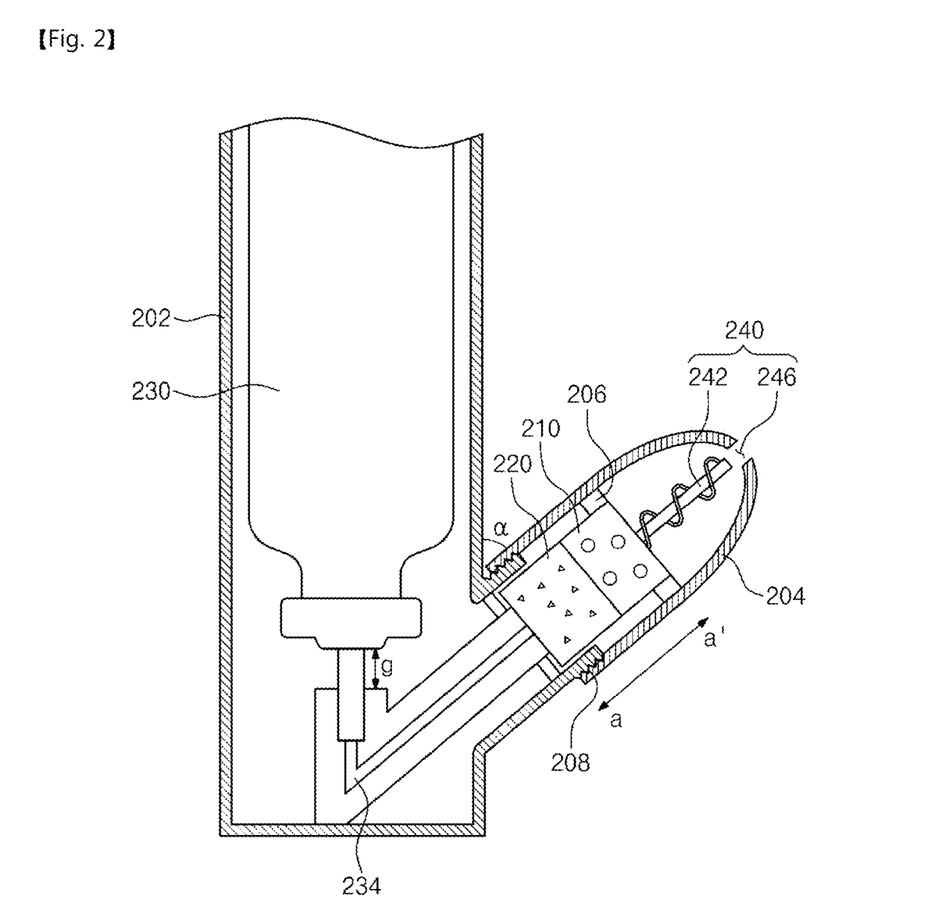
FIG. 2 is a view illustrating a drug delivery device according to an embodiment of the inventive concepts.

FIG. 2 is a view illustrating a drug delivery device according to an embodiment of the inventive concepts. In descriptions to components illustrated in FIG. 2, the descriptions to the same features as described with reference to FIG. 1 will be mentioned briefly.

Referring to FIG. 2, a drug delivery device according to an embodiment of the inventive concepts may include a freeze-dried drug container 210, a restoring solvent container 220, a compressor 230, and a spray unit 240. The freeze-dried drug container 210 of FIG. 2 may correspond to the freeze-dried drug container 210 of FIG. 1, the restoring solvent container 220 of FIG. 2 may correspond to the restoring solvent container 120 of FIG. 1, the compressor 230 of FIG. 2 may correspond to the compressor 130 of FIG. 1, and the spray unit 240 of FIG. 2 may correspond to the spray unit 140 of FIG. 1. Thus, detailed descriptions to the components 210, 220, 230 and 240 may be omitted for the purpose of ease and convenience in explanation.

In addition, the drug delivery device according to an embodiment of the inventive concepts may include a first housing 202 receiving the compressor 230, and a second housing 204 receiving the freeze-dried drug container 210, the restoring solvent container 220, and a membrane (not shown). Hereinafter, each of the components will be described in detail.

The first housing 202 may receive the compressor 230. A propellant movement path 234 may be provided on a bottom surface of the first housing 202. A compressed gas outlet of the compressor 230 may be inserted in the propellant movement path 234. A propellant (e.g., a compressed gas) from the compressor 230 may move through the propellant movement path 234.

In addition, when an operator pushes one end of the compressor 230, the compressor 230 may release the propellant while maximally moving by a distance 'g'. Since a movement distance of the compressor 230 is limited to the distance 'g', an one-time release amount of the propellant (i.e., the compressed gas) may be easily controlled.

Alternatively, the compressor 230 may be electronically controlled. In this case, an operator may press a button provided on an outer wall of a side of the first housing 202, thereby providing the propellant at a predetermined pressure. When an emergency situation occurs, it may be difficult for an operator to check the strength of force pressing the compressor 230. However, when the compressor 230 is electronically driven, an operator may press the button to easily provide the propellant at a predetermined pressure. Thus, convenience of operation and accuracy of medical treatment may be improved. The drug delivery device may include a battery to electronically control the compressor 230.

The first housing 202 may provide a receiving space to replace the compressor 230 with a new one. Thus, an operator may replace the compressor 230, depending on the degree of use of the compressor 230. Thus, the drug delivery device may be semipermanently used.

The second housing 204 may include the freeze-dried drug container 210, the membrane (not shown), and the restoring solvent container 220 and may provide the spray unit 240.

The spray unit 240 of the second housing 204 may provide a vent through which a drug is sprayed or injected. The spray unit 240 may include a spiral flow portion 242 and a spray hole 246 to effectively release or exhaust the drug. The spiral flow portion 242 may induce the drug to form a spiral stream when the thawed drug is sprayed. The spiral flow portion 242 may induce the drug to flow spirally unlike a case in which a drug flows linearly, and thus the drug may avoid a blood-brain barrier and may effectively reach a nose-to-brain drug delivery spot. For this end, the spiral flow portion 242 may have a single spiral structure or a double spiral structure. The spray hole 246 may release or exhaust the drug having the spiral stream by the spiral flow portion 242.

Since one end of the spray unit 240 is in direct contact with a nose (i.e., a nasal cavity), the one end of the spray unit 240 may be formed of a material harmless to the human body. For example, the one end of the spray unit 240 may be formed of stainless steel, in particular, stainless steel covered by a fluorinated ethylene propylene liner (FEP liner).

At this time, the thawed drug may be sprayed or injected through the spray hole 246 at a pressure of 6 psi to 20 psi, in particular, a pressure of 6 psi to 15 psi. If the pressure of the thawed drug sprayed or injected is less than 6 psi, the drug may not reach the nose-to-brain drug delivery spot. If the pressure of the thawed drug sprayed or injected is greater than 15 psi or 20 psi, a biomembrane may be damaged by the drug of the great pressure. The compressor 230 may electronically provide the propellant in such a way that the pressure of the thawed drug sprayed or injected through the spray hole 246 ranges from 6 psi to 20 psi, in particular, from 6 psi to 15 psi.

The second housing 204 may receive the restoring solvent container 220, the membrane (not shown), and the freeze-dried drug container 210 in the order named. In more detail, one end of the restoring solvent container 220 may be in contact with one end of the propellant movement path 234 into which the compressed gas (i.e., the propellant) of the compressor 230 is provided. Thus, the restoring solvent container 220, the membrane (not shown), the freeze-dried drug container 210 and the spray unit 240 of the drug delivery device may be located from the compressor 230 in the order named.

The second housing 204 may further include a sealing member 206 which seals and fixes the second housing 204 and the freeze-dried drug container 210. The sealing member 206 may fix the freeze-dried drug container 210 to the second housing 204, and thus the freeze-dried drug container 210 may not move with respect to the second housing 204. In addition, the sealing member 206 may prevent the drug, provided outward from the freeze-dried drug container 210, from being provided in other directions except a direction toward the spray hole 246 to flow backward.

The second housing 204 may be configured to be detachable from the first housing 202. For example, an inner surface of the second housing 204 may be screw-engaged with a screw thread 208 formed on an outer surface of the first housing 202. Thus, the second housing 204 may be coupled to and detachable from the first housing 202. Therefore, an operator may replace the freeze-dried drug container 210 and the restoring solvent container 220 depending on a spraying degree of the drug.

When the first housing 202 is coupled to the second housing 204, a longitudinal direction of the first housing 202 may form an acute angle a with a longitudinal direction of the second housing 204. Thus, one end of the second housing 204 may face an entrance of the nose (i.e., the nasal cavity) to improve convenience of operation of the drug delivery device.

The overall components of the drug delivery device according to an embodiment of the inventive concepts were described above with reference to FIG. 2. Hereinafter, a structure for storing a freeze-dried drug according to an embodiment of the inventive concepts will be described with reference to FIG. 3.

Figure 3:
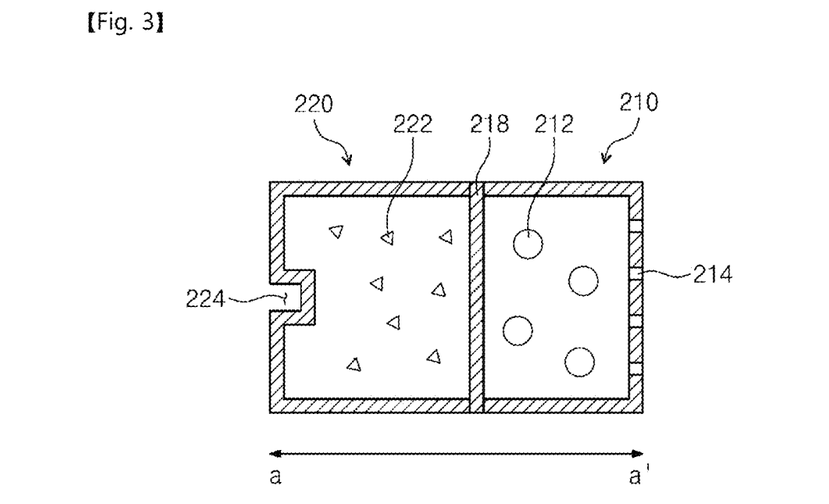
FIG. 3 is a view illustrating a structure for storing a freeze-dried drug, according to an embodiment of the inventive concepts.

FIG. 3 is a view illustrating a structure for storing a freeze-dried drug, according to an embodiment of the inventive concepts. FIG. 3 may be an enlarged view along a line a-a' of FIG. 2.

Referring to FIG. 3, a structure for storing a freeze-dried drug according to an embodiment of the inventive concepts may include a freeze-dried drug container 210, a restoring solvent container 220, and a membrane 218.

The freeze-dried drug container 210 may store a freeze-dried drug 212, as described above. The freeze-dried drug container 210 may include a fine hole 214 through which the freeze-dried drug is thawed and then is sprayed. A size of the fine hole 214 may be smaller than a particle size of the freeze-dried drug.

The restoring solvent container 220 may include a restoring solvent 222, as described above. The restoring solvent container 220 may include a receiving recess 224 in which one end of the propellant movement path 234 may be inserted. Thus, the compressed gas (i.e., the propellant) released through the propellant movement path 234 may be provided into the receiving recess 224 to press the restoring solvent container 220. Therefore, leakage of a driving force may be minimized.

The restoring solvent container 220 may be formed of, for example, a flexible material. Since the restoring solvent container 220 is formed of the flexible material, the freeze-dried drug 212 and the restoring solvent 222 may be mixed with each other. This will be described later in more detail.

The membrane 218 may be provided between the freeze-dried drug container 210 and the restoring solvent container 220 to prevent the freeze-dried drug 212 of the freeze-dried drug container 210 from being mixed with the restoring solvent 222 of the restoring solvent container 220.

The membrane 218 may have a dense structure to prevent the freeze-dried drug 212 of the freeze-dried drug container 210 from being mixed with the restoring solvent 222 of the restoring solvent container 220 when the drug is stored. In addition, since the membrane 218 should be removed to mix the freeze-dried drug 212 with the restoring solvent 222 when the drug is sprayed, the membrane 218 may have a thin film structure which may be easily broken in a thickness direction of the membrane 218.

Thus, the drug delivery device according to an embodiment of the inventive concepts may store the freeze-dried drug 212 and the restoring solvent 222 separately from each other, such that the freeze-dried drug 212 is not mixed with the restoring solvent 222 for thawing the freeze-dried drug 212.

The structure for storing a freeze-dried drug according to an embodiment of the inventive concepts was described above with reference to FIG. 3. Hereinafter, a process of spraying a freeze-dried drug according to an embodiment of the inventive concepts will be described with reference to FIGS. 4A and 4B.

Figure 4A:
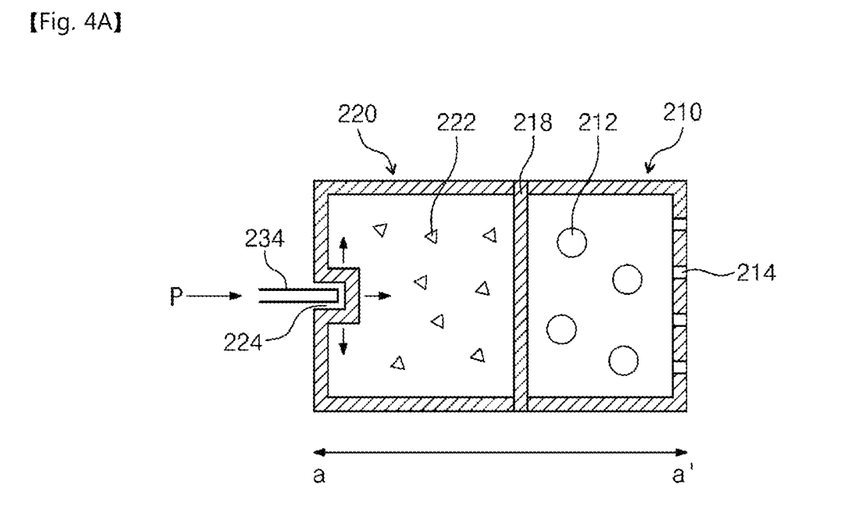
FIGS. 4A and 4B are views illustrating a process of spraying a freeze-dried drug, according to an embodiment of the inventive concepts.
Figure 4B:
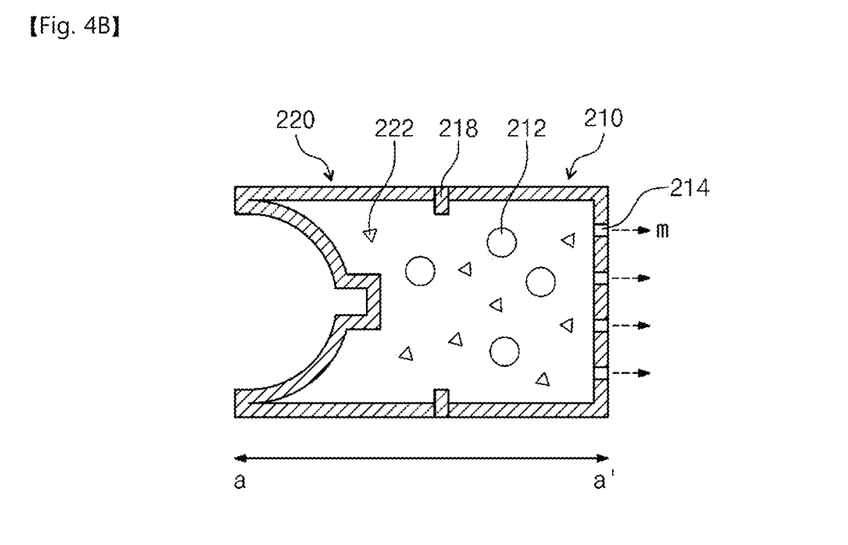

FIGS. 4A and 4B are views illustrating a process of spraying a freeze-dried drug, according to an embodiment of the inventive concepts. FIGS. 4A and 4B may be an enlarged view along the line a-a' of FIG. 2.

Referring to FIG. 2 and FIG. 4A, when the compressed gas of the compressor 230 is released to spray the drug, the compressed gas may provide compression force P to the receiving recess 224 of the restoring solvent container 220 through the propellant movement path 234.

Referring FIG. 4B, the restoring solvent container 220 formed of the flexible material may be deformed by the provided compression force P. An internal pressure of the restoring solvent container 220 may be increased by the deformation of the restoring solvent container 220. The increased internal pressure may open the membrane 218, and thus the restoring solvent 222 of the restoring solvent container 220 may be mixed with the freeze-dried drug 212 of the freeze-dried drug container 210. As a result, the freeze-dried drug 212 may be thawed and restored, and the thawed drug may be released through the fine hole 214. At this time, the thawed drug may be released (m) through the fine hole 214 by pressure increased through volume expansion in the thawing process and by the driving force provided from the compressed gas of the compressor 230. The drug released through the fine hole 214 may be sprayed into the nose (i.e., the nasal cavity) through the spiral flow portion 242 and the spray hole 246.

Meanwhile, in a certain embodiment, the freeze-dried drug container 210 described with reference to FIGS. 3 and 4 may not include the fine hole 214. In this case, a wall of the freeze-dried drug container 210 which is adjacent to the spray unit 240 may be formed of a partition wall which is breakable by the compressed gas. At this time, the partition wall may be more rigid than the membrane 218, such that the partition wall is opened after the membrane 218 is opened.

The process of spraying the freeze-dried drug according to an embodiment of the inventive concepts was described above with reference to FIGS. 4A and 4B. Hereinafter, a structure for storing a freeze-dried drug according to another embodiment of the inventive concepts will be described with reference to FIG. 5.

Figure 5:
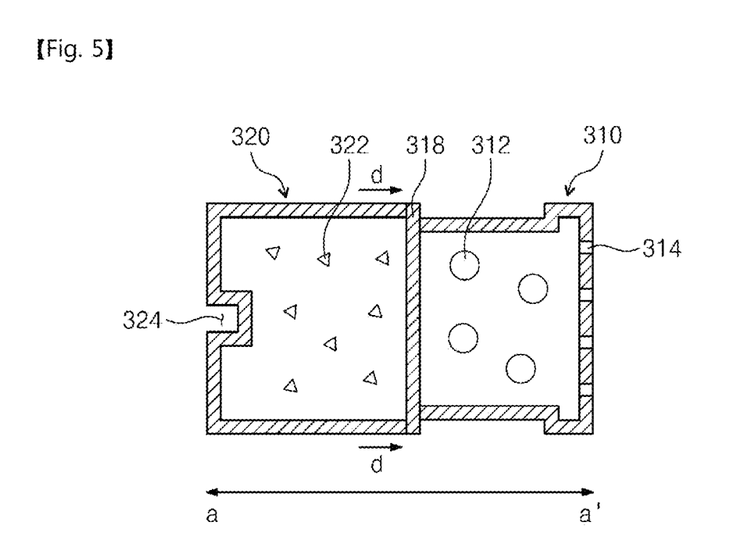
FIG. 5 is a view illustrating a structure for storing a freeze-dried drug, according to another embodiment of the inventive concepts.

FIG. 5 is a view illustrating a structure for storing a freeze-dried drug, according to another embodiment of the inventive concepts. FIG. 5 may be an enlarged view along the line a-a' of FIG. 2.

Referring to FIG. 5, a structure for storing a freeze-dried drug according to another embodiment of the inventive concepts may include a freeze-dried drug container 310, a restoring solvent container 320, and a membrane 318.

The freeze-dried drug container 310 may store a freeze-dried drug 312, as described above. The freeze-dried drug container 310 may include a fine hole 314 through which the freeze-dried drug is thawed and then is sprayed. A size of the fine hole 314 may be smaller than a particle size of the freeze-dried drug.

The restoring solvent container 320 may include a restoring solvent 322, as described above. The restoring solvent container 320 may include a receiving recess 324 in which one end of the propellant movement path 234 may be inserted. Thus, the compressed gas (i.e., the propellant) released through the propellant movement path 234 may be provided into the receiving recess 324 to press the restoring solvent container 320. Therefore, leakage of a driving force may be minimized.

The restoring solvent container 320 may be formed of, for example, a rigid material. Since the restoring solvent container 320 is formed of the rigid material, the freeze-dried drug 312 and the restoring solvent 322 may be mixed with each other. This will be described later in more detail.

The membrane 318 may be provided between the freeze-dried drug container 310 and the restoring solvent container 320 to prevent the freeze-dried drug 312 of the freeze-dried drug container 310 from being mixed with the restoring solvent 322 of the restoring solvent container 320.

The membrane 318 may have a dense structure to prevent the freeze-dried drug 312 of the freeze-dried drug container 310 from being mixed with the restoring solvent 322 of the restoring solvent container 320 when the drug is stored. In addition, since the membrane 318 should be removed to mix the freeze-dried drug 312 with the restoring solvent 322 when the drug is sprayed, the membrane 318 may have a thin film structure which may be easily broken in a thickness direction of the membrane 218.

Thus, the drug delivery device according to another embodiment of the inventive concepts may store the freeze-dried drug 312 and the restoring solvent 322 separately from each other, such that the freeze-dried drug 312 is not mixed with the restoring solvent 322 for thawing the freeze-dried drug 312.

The structure for storing a freeze-dried drug according to another embodiment of the inventive concepts was described above with reference to FIG. 5. Hereinafter, a process of spraying a freeze-dried drug according to another embodiment of the inventive concepts will be described with reference to FIGS. 6A and 6B.

Figure 6A:
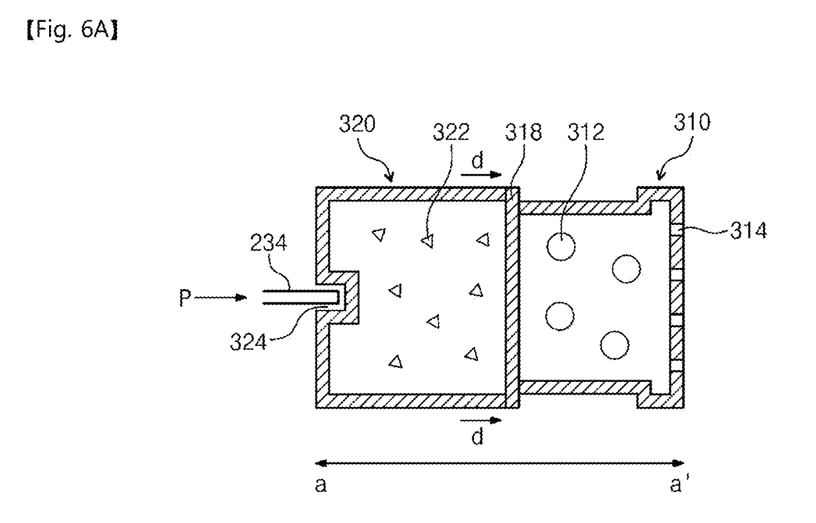
FIGS. 6A and 6B are views illustrating a process of spraying a freeze-dried drug, according to another embodiment of the inventive concepts.
Figure 6B:
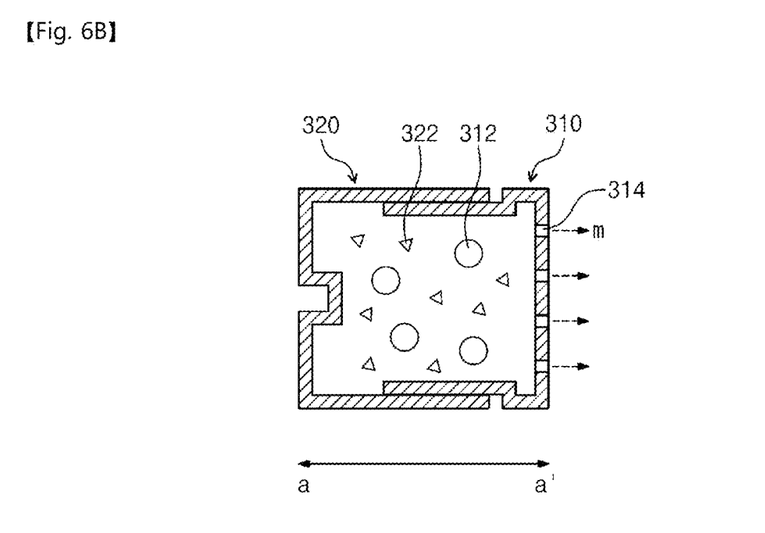

FIGS. 6A and 6B are views illustrating a process of spraying a freeze-dried drug, according to another embodiment of the inventive concepts. FIGS. 6A and 6B may be an enlarged view along the line a-a' of FIG. 2.

Referring to FIG. 2 and FIG. 6A, when the compressed gas of the compressor 230 is released to spray the drug, the compressed gas may provide compression force P to the receiving recess 324 of the restoring solvent container 320 through the propellant movement path 234.

Referring to FIG. 6B, the restoring solvent container 320 formed of the rigid material may be moved in a direction 'd' toward the freeze-dried drug container 310 by the provided compression force P. For example, the restoring solvent container 320 may be moved in such a way that an inner sidewall of the restoring solvent container 320 slides along an outer sidewall of the freeze-dried drug container 310. An internal pressure of the restoring solvent container 320 may be increased by the movement of the restoring solvent container 320. The increased internal pressure may open the membrane 318, and thus the restoring solvent 322 of the restoring solvent container 320 may be mixed with the freeze-dried drug 312 of the freeze-dried drug container 310. As a result, the freeze-dried drug 312 may be thawed and restored, and the thawed drug may be released through the fine hole 314. At this time, the thawed drug may be released (m) through the fine hole 314 by pressure increased through volume expansion in the thawing process and by the driving force provided from the compressed gas of the compressor 230. The drug released through the fine hole 314 may be sprayed into the nose (i.e., the nasal cavity) through the spiral flow portion 242 and the spray hole 246.

Meanwhile, in a certain embodiment, the freeze-dried drug container 310 described with reference to FIGS. 5 and 6A-6B may not include the fine hole 314. In this case, a wall of the freeze-dried drug container 310 which is adjacent to the spray unit 240 may be formed of a partition wall which is breakable by the compressed gas. At this time, the partition wall may be more rigid than the membrane 218, such that the partition wall is opened after the membrane 218 is opened.

The process of spraying the freeze-dried drug according to another embodiment of the inventive concepts was described above with reference to FIGS. 6A and 6B. In the structures for storing the freeze-dried drug and the processes of spraying the drug described with reference to FIGS. 3 to 6B, the compressed gas of the compressor 230 may act as a mixing trigger of the freeze-dried drug and the restoring solvent. Alternatively, a button for instructing mixing of the freeze-dried drug and the restoring solvent may be provided, and an operator may press the button to start mixing of the freeze-dried drug and the restoring solvent.

Hereinafter, a method of using a drug delivery device according to an embodiment of the inventive concepts will be described with reference to FIG. 7.

Figure 7:
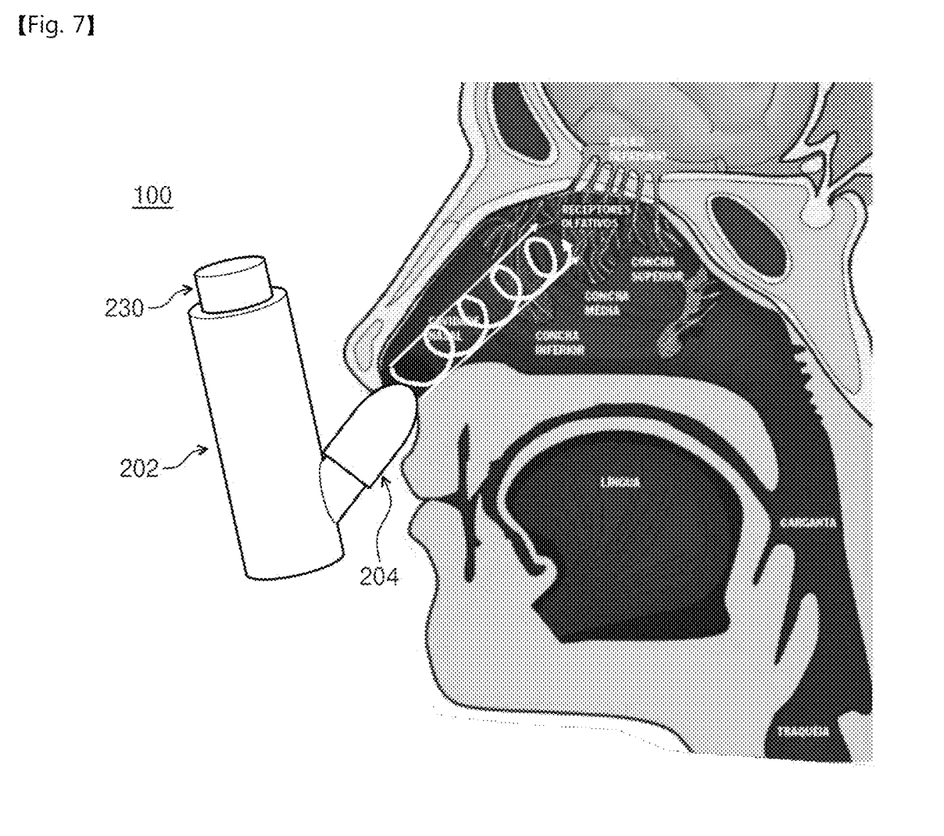
FIG. 7 is a view illustrating a method of using a drug delivery device according to an embodiment of the inventive concepts.

FIG. 7 is a view illustrating a method of using a drug delivery device according to an embodiment of the inventive concepts. The using method described with reference to FIG. 7 may be applied to both the drug storing structure illustrated in FIG. 3 and the drug storing structure illustrated in FIG. 5.

Referring to FIG. 7, one end of the drug delivery device 100 according to an embodiment of the inventive concepts may be inserted in an entrance of a nose (i.e., a nasal cavity). The compressor 230 may be pushed in the state where the one end of the drug delivery device 100 is inserted in the entrance of the nose, and thus a drug stored in a freeze-dried form may be thawed and may be sprayed into the nose in a spiral form (see a white arrow). The drug sprayed into the nose may accurately reach a nose-to-brain drug delivery spot to improve a nose-to-brain drug delivery rate. At this time, a drug delivery efficiency of the drug delivery device 100 may be affected by a drug injection position of the human body and a drug injection pressure (or a drug spray pressure). Hereinafter, a nose-to-brain drug delivery efficiency related to the drug injection position of the human body will be described with reference to FIGS. 8 to 10, and a nose-to-brain drug delivery efficiency related to the drug injection pressure will be described with reference to FIG. 11.

Figure 8:
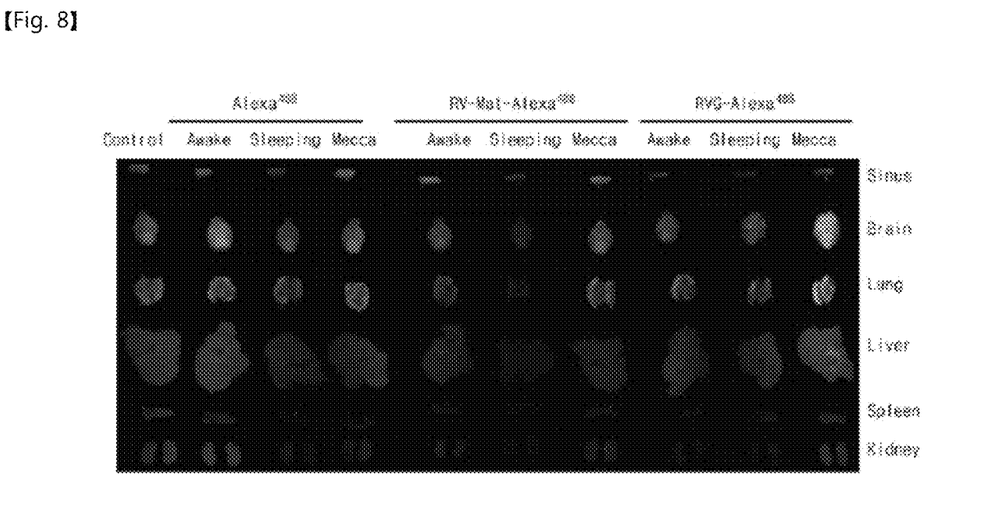
FIGS. 8 to 10 show experimental results for explaining a nose-to-brain drug delivery efficiency depending on a position, according to an embodiment of the inventive concepts.
Figure 9:
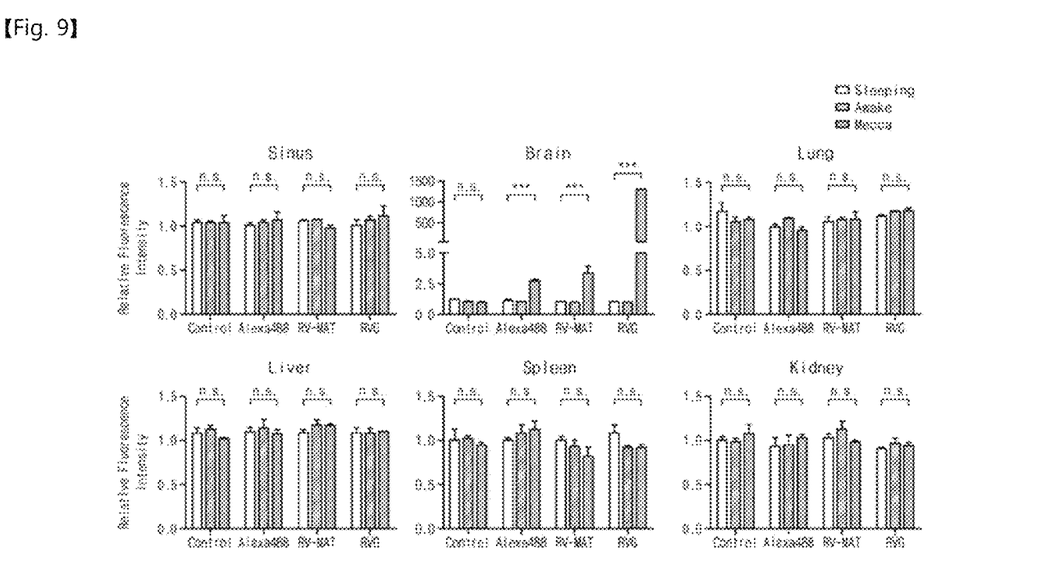
Figure 10:
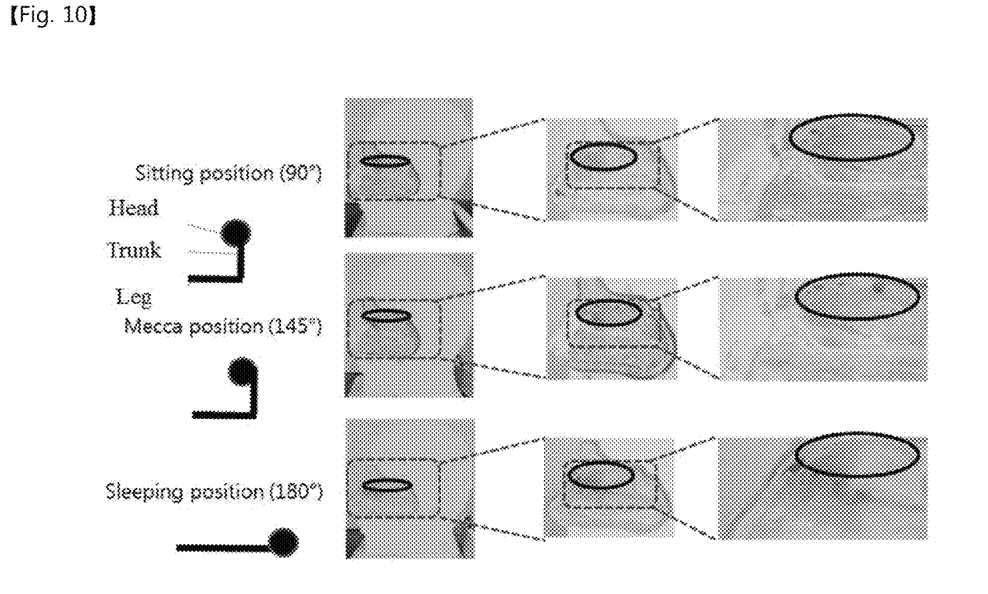

FIGS. 8 to 10 show experimental results for explaining a nose-to-brain drug delivery efficiency depending on a position, according to an embodiment of the inventive concepts.

When the drug delivery device according to an embodiment of the inventive concepts is used, to maximize a nose-to-brain drug delivery effect, the drug delivery device may be used in a state where an object (e.g., a head of a subject) is maintained in a mecca position. When a drug is injected in the mecca position, the drug may be intensively delivered to a brain through a nose to inhibit or prevent the drug from being provided to other organs. Here, the mecca position may mean a position in which the head of the subject faces the chest thereof. In addition, in using the drug delivery device according to an embodiment of the inventive concepts, the mecca position of the object (e.g., the subject) may be induced when the subject is in an unconscious state or a sleep state, and then, the drug may be provided. In this case, the drug may be effectively provided.

FIGS. 8 and 9 show test results of nose-to-brain drug delivery according to drug injection through a non-mecca position and drug injection through a mecca position according to an embodiment of the inventive concepts.

In the test results shown in FIGS. 8 and 9, Alexa488, RVG peptide labeled with Alexa488, and RV-MAT labeled with Alexa488 were used as the markers.

In addition, a sleeping (i.e., unconscious) experimental animal in a non-mecca position, a non-sleeping experimental animal in the non-mecca position, and a sleeping experimental animal in the mecca position were prepared to check effects of the nose-to-brain drug delivery in the mecca position. In FIGS. 8 and 9, the sleeping experimental animal in the non-mecca position is represented as 'Sleeping', the non-sleeping experimental animal in the non-mecca position is represented as 'Awake', and the sleeping (and unconscious) experimental animal in the mecca position is represented as 'Mecca'.

In the present test, Alexa488, RVG peptide labeled with Alexa488, and RV-MAT labeled with Alexa488 used as the markers were injected into the experimental animals in the Sleeping state, the Awake state and the Mecca state through their noses.

As a result, in other organs, there was substantially no difference in the injection degree of the drug depending on the position of the experimental animal. However, the drug was injected to the brain of the experimental animal in the mecca position (see degree of fluorescence expression), but the drugs were not injected to the brains of the experimental animals in the non-mecca positions. In particular, it may be recognized that the degree of the fluorescence expression is excellent when the sleeping experimental animal is in the mecca position.

In addition, referring to FIG. 10, nose-to-brain drug delivery was performed to a human body model in each of a sitting position, a mecca position and a sleeping position thereof. As shown in FIG. 10, it may be recognized that a nose-to-brain drug delivery amount is great in the mecca position.

In other words, it may be recognized that the mecca position (in particular, the mecca position in a sleep state) is a substantially unique position capable of performing the nose-to-brain drug delivery. As a result, the drug delivery device according to an embodiment of the inventive concepts may inject a drug through the nose in a state where an object (e.g., a human body) takes the mecca position (in particular, in the sleep state), and thus the drug may be effectively delivered to the brain.

Figure 11:
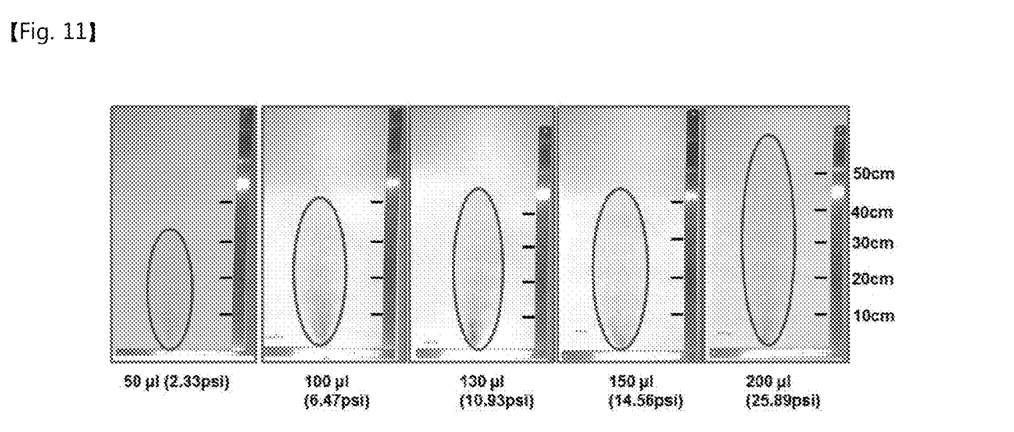
FIG. 11 shows experimental results for explaining a nose-to-brain drug delivery efficiency depending on a drug injection pressure, according to an embodiment of the inventive concepts.

FIG. 11 shows experimental results for explaining a nose-to-brain drug delivery efficiency depending on a drug injection pressure, according to an embodiment of the inventive concepts.

Referring to FIG. 11, an injection pressure (i.e., a pressure at an outlet of the spray hole 246) of the drug delivery device according to an embodiment of the inventive concepts may range from 6 psi to 20 psi, in particular, from 6 psi to 15 psi. In FIG. 11, when the injection pressure (or the spray pressure) ranges from 6 psi to 20 psi, the drug may be delivered to the brain by the sufficiently high injection pressure and damage of a biomembrane may also be prevented.

In other words, the drug delivery device according to an embodiment of the inventive concepts may provide the propellant to spray or inject the drug at the pressure of 6 psi to 20 psi, and thus the nose-to-brain drug delivery efficiency may be improved. In addition, the compressor providing the propellant may be configured to be electronically operated, and thus the convenience of the operation of the drug delivery device may be improved and the drug delivery device may be effectively used in emergency situations.

The drug delivery device according to the embodiments described with reference to FIGS. 1 to 11 may store a drug in the freeze-dried state. Thus, since the drug from which water is removed is stored, activity of bacteria or enzymes may be inhibited and deterioration of the drug may be minimized. On the contrary, if a drug is stored in a liquid state, the drug may be deteriorated by activity of bacteria or enzymes. Thus, a pharmacological effect may be limited and secondary diseases may be caused. However, the drug delivery device according to an embodiment of the inventive concepts may store the freeze-dried drug to improve preservation of the drug.

In addition, the drug delivery device according to an embodiment of the inventive concepts may store both the freeze-dried drug and the restoring solvent for thawing and restoring the freeze-dried drug. In other words, when the drug is sprayed, the freeze-dried drug and the restoring solvent which are stored together may be mixed with each other to thaw the freeze-dried drug. In more detail, in spraying the drug, only the compressor may be operated to thaw the freeze-dried drug and to provide the driving force for spraying the thawed drug, and thus ease and convenience of use may be improved or maximized.

Moreover, in the drug delivery device according to an embodiment of the inventive concepts, the compressor may be detachable from the first housing, and the freeze-dried drug container and the restoring solvent container may be detachable from the second housing. Thus, convenience of replacement or exchange may be improved and the drug delivery device may be semipermanently used.

In the embodiments described above, the nose-to-brain drug delivery devices were described as examples. However, the features and/or the scopes of the embodiments of the inventive concepts may be applied to a simple nose drug delivery device and/or an oral drug delivery device.

In addition, the drug delivery device according to an embodiment of the inventive concepts may spray or inject the drug at a predetermined pressure (e.g., the pressure of 6 psi to 20 psi) to improve the nose-to-brain drug delivery efficiency. Furthermore, the drug delivery device according to an embodiment of the inventive concepts may inject the drug through the nose in a state where an object is in the mecca position, thereby improving the nose-to-brain drug delivery efficiency.

In particular, in conventional arts, a membrane of a skin may be broken by a typical device for delivering a drug to an olfactory region. In addition, patients may inhale drugs in a conscious state in nose-to-brain delivery, and thus the drugs may be mainly provided to lungs, not brains. Moreover, nose-to-brain drug delivery itself may be difficult. Furthermore, when pressure is manually provided in an emergency situation, a delivery amount of a drug may be varied depending on an operator by a difference in injection pressure. However, according to the aforementioned embodiments of the inventive concepts, the drug may be effectively delivered to the brain through the nose by the control of the drug injection pressure of the drug delivery device according to the inventive concepts and the induction of the position of an object according to the inventive concepts.

According to the embodiments of the inventive concepts, the nose-to-brain drug delivery device may include the freeze-dried drug container for storing the freeze-dried drug, the restoring solvent container for storing the solvent for thawing the freeze-dried drug, the membrane for preventing the freeze-dried drug from being mixed with the solvent, and the compressor for providing the driving force. The membrane may be opened by the driving force of the compressor to mix the freeze-dried drug with the solvent, thereby thawing the freeze-dried drug, and the thawed drug may be sprayed by the driving force of the compressor. Thus, the drug may be stored in the freeze-dried state to minimize influence of bacteria or enzymes on the drug.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A nose-to-brain drug delivery device comprising:
    a freeze-dried drug container for storing a freeze-dried drug;
    a restoring solvent container for storing a solvent for reconstituting the freeze-dried drug;
    a membrane for preventing the freeze-dried drug from being mixed with the solvent; and
    a compressor for providing a driving force,
    wherein the membrane is opened by the driving force of the compressor to mix the freeze-dried drug with the solvent, thereby reconstituting the freeze-dried drug, and the reconstituted drug is capable of being sprayed by the driving force of the compressor,
    wherein the reconstituted drug is capable of being sprayed into a nose of a subject in a mecca position state where a head of the subject faces a chest of the subject,
    wherein a propellant movement path is provided between the compressor and the restoring solvent container and provides a flow path for compressed gas stored in the compressor,
    wherein the restoring solvent container is formed of a flexible material and is deformed by the driving force to increase an internal pressure of the restoring solvent container, and the membrane is capable of being opened by the increased internal pressure,
    wherein one end of the restoring solvent container includes a receiving recess in which one end of the propellant movement path is inserted, and
    wherein the compressed gas released from the one end of the propellant movement path into the receiving recess is capable of pushing the one end of the restoring solvent container in at least two directions.

2. The nose-to-brain drug delivery device of claim 1, wherein the compressor provides the driving force to the one end of the restoring solvent container, and another end of the restoring solvent container is blocked by the membrane so as to be separated from the freeze-dried drug container.

3. The nose-to-brain drug delivery device of claim 1, wherein the freeze-dried drug container includes a fine hole for spraying the reconstituted drug.

4. The nose-to-brain drug delivery device of claim 3, further comprising:
    a spray unit,
    wherein the drug released from the fine hole is capable of being sprayed outward through the spray unit.

5. The nose-to-brain drug delivery device of claim 1, wherein the restoring solvent container, the membrane, and the freeze-dried drug container are disposed in the order named, from the compressor.

6. The nose-to-brain drug delivery device of claim 1, further comprising:
    a first housing in which the compressor is received; and
    a second housing in which the restoring solvent container, the membrane, and the freeze-dried drug container are received,
    wherein the second housing is detachable from the first housing, and a longitudinal direction of the first housing forms an acute angle with a longitudinal direction of the second housing when the first housing is coupled to the second housing.

7. The nose-to-brain drug delivery device of claim 1, wherein a spray pressure of the reconstituted drug ranges from 6 psi to 20 psi.

8. The nose-to-brain drug delivery device of claim 7, wherein the spray pressure of the reconstituted drug ranges from 6 psi to 15 psi.

* * * * *